(12) United States Patent  
Chou et al.

(10) Patent No.: US 7,727,370 B2  
(45) Date of Patent: ***Jun. 1, 2010

(54) REFERENCE PH SENSOR, PREPARATION AND APPLICATION THEREOF

(75) Inventors: Jung-Chuan Chou, Douliou (TW); Diing-Jia Tzeng, Nantou County (TW)

(73) Assignee: National Yunlin University of Science and Technology, Yunlin (TW)

( * ) Notice: Subject to any disclaimer, the term of this patent is extended or adjusted under 35 U.S.C. 154(b) by 0 days.

This patent is subject to a terminal disclaimer.

(21) Appl. No.: 12/397,231

(22) Filed: Mar. 3, 2009

(65) Prior Publication Data

US 2009/0170207 A1  Jul. 2, 2009

Related U.S. Application Data

(62) Division of application No. 11/448,478, filed on Jun. 7, 2006, now Pat. No. 7,582,500.

(30) Foreign Application Priority Data

Jan. 4, 2006  (TW)  ............................... 95100302 A

(51) Int. Cl.  
G01N 27/26  (2006.01)

(52) U.S. Cl. ...................................... 204/433; 257/253

(58) Field of Classification Search ................. 204/433, 204/416, 192.17; 257/253, 414, 40; 438/48–49, 438/99  
See application file for complete search history.

(56) References Cited

U.S. PATENT DOCUMENTS

| | | | | |
|---|---|---|---|---|
| 5,296,122 A * | 3/1994 | Katsube et al. | ........ | 204/298.04 |
| 5,309,085 A * | 5/1994 | Sohn | .......................... | 257/253 |
| 5,384,028 A * | 1/1995 | Ito | .............................. | 257/253 |
| 5,602,467 A * | 2/1997 | Krauss et al. | ............... | 324/71.1 |
| 5,911,873 A * | 6/1999 | McCarron et al. | ........... | 205/789 |
| 6,218,208 B1 * | 4/2001 | Chou et al. | .................... | 438/49 |
| 6,251,246 B1 * | 6/2001 | Chan | .......................... | 204/418 |
| 6,326,215 B1 * | 12/2001 | Keen | .......................... | 436/518 |
| 6,409,909 B1 * | 6/2002 | Spichiger-Keller et al. | ....................... | 205/777.5 |
| 7,431,811 B2 * | 10/2008 | Chou et al. | ................. | 204/291 |
| 7,598,546 B1 * | 10/2009 | Chou et al. | ................. | 257/253 |
| 2005/0147736 A1 * | 7/2005 | Hsiung et al. | ................. | 427/58 |
| 2007/0095664 A1 * | 5/2007 | Chou et al. | ................. | 204/433 |

* cited by examiner

*Primary Examiner*—Savitri Mulpuri  
(74) *Attorney, Agent, or Firm*—Quintero Law Office

(57) ABSTRACT

A reference pH sensor, the preparation and application thereof. The reference pH sensor is an extended gate field effect transistor (EGFET) structure and comprises a metal oxide semiconductor field effect transistor (MOSFET) on a semiconductor substrate, a sensing unit comprising a substrate, a solid-state conductive sensing layer on the substrate, and a polypyrrole layer on the solid-state conductive sensing layer, and a metal wire connecting the MOSFET and the sensing unit.

8 Claims, 8 Drawing Sheets

REFERENCE PH SENSOR, PREPARATION AND APPLICATION THEREOF

This application is a divisional of U.S. application Ser. No. 11/448,478, filed Jun. 7, 2006, the entire disclosure of which is hereby incorporated by reference.

BACKGROUND OF THE INVENTION

1. Field of the Invention

The present invention relates to a pH sensor, and in particular to a planar solid-state reference electrode of a pH sensor.

2. Description of the Related Art

Since there are many drawbacks to the practical application of the conventional organic quantitative analysis, such as complicated operation, long analysis time, expensive equipments, inapplicability for the detection of a continuous process and the like. [J. U. Chen, Biological Industry, Vol. 4(3), 1993, pp. 205-212; D. G. Huang, W. S. Chen, and R. C. Hsu, Biological Industry, Vol. 7(4), 1996, pp. 291-298; S. Zhang, G. Wright, and Y. Yang, Biosensors and Bioelectronics, Vol. 15, 2000, pp. 273-282] Studies to discover a solution that can overcome disadvantages associated with the conventional quantitative analysis have been carried out. As a result, a biosensor is designed by combining the theories of biochemistry, electrical circuit, material science, and optics to meet the requirements of various fields.

The ion-sensitive field effect transistor (ISFET) was first disclosed by P. Bergveld in 1970 [P. Bergveld, IEEE Tran. on Biomed. Eng., Vol. BME-17, 1970, pp. 710-714]. The device is a product of applied electrochemistry and microelectronics, and has an ion selection function and FET properties. The ion-sensitive device is strictly different from the conventional ion selection electrode. The ISFET is a semiconductor pH sensor in which the metal on the gate of the metal-oxide semiconductor field effect transistor (MOSFET) is removed to expose the silicon dioxide layer. When the ISFET is placed into an aqueous solution, the exposed silicon dioxide layer detects the Zeta potential produced from the aqueous solution such that the purpose of sensing the ion concentration in the aqueous solution can be achieved. The related studies on ISFET, such as material improvement [Manuela Adami et al., Sensors and Actuators B, Vol. 24-25, 1995, pp. 889-893; A. S. Poghossian et al., Sensors and Actuators B, Vol. 7, 1992, pp. 367-370; T. Katsube et al., Sensors and Actuators B, Vol. 2, 1982, pp. 399-410], the study and miniaturization of reference electrodes [S. D. Collins et al., Sensors and Actuators B, Vol. 10, 1993, pp. 169-178; Yuri G. Vlasov, Andrey V. Bratov, Sensors and Actuators B, Vol. 10, 1992, pp. 1-6; C. Diekmann et al., Sensors and Actuators B, Vol. 24-25, 1995, pp. 276-278], the improvement of structures [C. Cane et al., Sensors and Actuators B, Vol. 35-36, 1996, pp. 136-140; Pavel Neuzil et al., Sensors and Actuators B, Vol. 24-25, 1995, pp. 232-235] and the like have been discussed.

An extended gate field effect transistor (EGFET) is an element developed from ISFET, provided firstly by J. Spiegel [J. Van Der Spiegel et al., Sensors and Actuators, Vol. 4, 1983, pp. 291-298], and unlike ISFET, the EGFET preserves the original gate in the MOSFET and has a sensing membrane plated on the other end extended from the metal gate. Compared with ISFET, the EGFET has the following advantages: (1) electrostatic protection is provided by the conductive wire on the element; (2) elimination of direct contact between the transistor of the element and the aqueous solution; (3) the effect of light on the element being reduced [P. Bergveld and A. Sibbald, "Analytical and Biomedical Application of Ion-Sensitive Field Effect Transistor", published by Elsevier science, New York, 1988, pp. 2-60].

A reference electrode is a type of electrochemical sensing device, which is an electrode used to establish a standard reference potential corresponding to the different standard potential of the solution to be detected. The feature of the reference electrode is that the surface potential of the reference electrode remains stable in different solutions and avoids deviation of the sensitivity of the sensing device caused by different detected solutions. A reference electrode commonly used on an ordinary electrochemical sensing device is a calomel electrode or a silver/silver chloride electrode, but most reference electrodes are wet reference electrodes, and therefore, those reference electrodes cannot be miniaturized, and must be immersed into an associated buffer solution for a long period, which is inconvenient both for its use and storage. Hence, in order to achieve the objects of miniaturized fabrication and dry storage, the reference electrode design is an important subject of study and there are many related articles having discussions regarding this aspect. Referring to articles on pH ISFET, it is found that the miniaturization of a reference electrode is a present tendency of the sensing device development, while current methods of fabrication include: micro-electromechanical processing, silver/silver chloride membrane deposition, differential pair circuit design [Huixian Zhu et al., Sensors and Actuators B, Vol. 46, 1998, pp. 155-159; Joseph J. Pancrazio et al., Biosensors and Bioelectronics, Vol. 13, 1998, pp. 971-979; N. Zine et al., "Multisensor Silicon Needle for Cardiac Applications", Proceedings of The 1st Annual International Conference on Microtechnologies in Medicine and Biology, 2000, pp. 216-219 R. J. Reay et al., "An Integrated CMOS Potentiostat for Miniaturized Electroanalytical Instrumentation", Proceedings of the IEEE International Solid-State Circuits Conference, 1994, pp. 162-163].

Patents disclosing conventional techniques include: U.S. Pat. No. 6,251,246 to Andy D. C. Chan discloses a material for establishing solid-state contact for ion selective electrodes which is a polymeric material forming a stable, reproducible interface between the ionic and electronic domains of an ion selective sensor, or an ion selective field effect transistor, or the like. When employed in an ion selective sensor, the polymeric material provides a solid internal reference electrode and an ion selective material. U.S. Pat. No. 6,218,208 to the inventors discloses fabrication of a multi-structure ion sensitive field effect transistor with a pH sensing layer of a tin oxide thin film. The multi-structure ISFET has high performances such as a linear pH sensitivity of approximately about 56-58 mV/pH in a concentration range between pH 2 and pH 10, a low drift value of approximately 5 mV/day, and response time of less than 0.1 seconds. This device has other advantages, such as the inexpensive fabrication system, low cost, and mass production.

U.S. Pat. No. 5,309,085 to Byung Ki Sohn discloses a measuring circuit with a biosensor utilizing ion sensitive field effect transistors. The circuit has advantages of being a simple structure and easy to integrate, which comprises two ISFETs as inputs, one is an enzyme field effect transistor (enzyme EFT), and the other is the reference FET. The circuit has various amplification functions to amplify the sensed output of the sensing device. The voltage variation of ISFET was raised through using an unsteady semi-reference electrode that could be affected by the change of the temperature, so that the working characteristic of the device could be adjusted by changing the gain of read-out circuit. The ISFET biosensor can be provided on a single chip in combination with a measuring circuit to achieve the miniaturization of the sensing device. U.S. Pat. No. 5,296,122 to Teruaki Katsube, Shuichiro Yamaguchi, Naoto Uchida, and Takeshi discloses an apparatus for forming thin film which is a hydrophobic membrane to be used as the reference electrode of an ISFET. The hydrophobic membrane is grown on a substrate by neutral plasma deposition or by sputtering. The apparatus includes a vacuum chamber, an atom beam generator, a target base, and a shield for growth controlling. The thin membrane was suitable for an ion sensor, such as an ISFET, and an enzyme sensor.

U.S. Pat. No. 4,641,084 to Satsuki Komatsu discloses an apparatus for measuring ion concentration of a specific ion contained in a test liquid. The measurement is performed with the aid of a reference electrode and an ion sensitive field effect transistor having a gate portion selectively sensitive to the specific ion, including a series circuit of a reference resistor and a constant voltage supply source connected across drain and source of the ion sensitive field effect transistor, a potential control circuit having inputs connected across the reference resistor to detect a potential difference across the reference resistor for controlling a source or drain potential of the ion sensitive field effect transistor, in such a manner that the potential difference remains at a predetermined value, and a voltmeter for measuring the source or drain potential as a measure of the ion concentration. In addition, U.S. Pat. No. 5,602,467 to Mathias Krauss, Beate Hildebrandt, Christian Kunath, and Eberhard Kurth discloses a circuit for measuring ion concentrations in solutions. A framework for measuring the ion concentration in the solution by using an ISFET circuit layout is provided. The circuit layout could expose the gate voltage difference of the FET and the parameter/environmental deviation caused by operation factors. The circuit layout comprises two measurement/test amplifiers, two ISFETs, and two identical FETs. The two ISFETs are connected to the two FET respectively, and the output from the first amplifier displays the gate voltage change between two ISFETs and FETs, and the second amplifier displays the output difference of two ISFET. The output of the first amplifier is the ground reference electrode that connected to 4 reference electrodes. Thus, the framework is capable of detecting the ion concentration.

U.S. Pat. No. 4,882,292 to Ernst J., and Maria D. discloses a process for manufacturing a REFET or a CHEMFET. The process for manufacturing a REFET and/or CHEMFET comprises (a) covalent bonding of a hydrophilic polymer layer to an isolator layer applied to a semiconductor material; (b) the absorption of water or an aqueous solution into said hydrophilic polymer layer; and (c) the binding of a hydrophobic polymer layer to the water holding hydrophilic polymer layer.

U.S. Pat. No. 5,684,619 to Shabrang Mani, Babinec Susan J., and Varjian Richard D. discloses an improved electrochromic device. The improved electrochromic device has an electrochromic electrode in contact with an ion conductor, and the ion conductor in turn being in contact with a layer of gold. The improvement is to interpose a layer of ruthenium oxide between the ion conductor and the layer of gold. The layer of ruthenium oxide is not an electrochromic material.

From these disclosures, it can be seen that the conventional techniques still have many drawbacks and are not designed well, and the improvement for a solid-state dry reference electrode and a planar sensing device framework is still required.

BRIEF SUMMARY OF THE INVENTION

A detailed description is given in the following embodiments with reference to the accompanying drawings.

In view of the disadvantages of the conventional sensing devices, the inventors are determined to improve and innovate, and, after studying intensively for many years, have successfully developed a process for fabrication of a new planar solid-state reference electrode. The prepared reference pH sensor can be designed as a differential pH sensor having a pyrrole/$RuO_X$/Si substrate with a lower pH sensitivity in combination with a $RuO_X$/Si substrate as a standard electrode to provide a standard potential of an electrolyte. The planar reference electrode provides the advantages of the miniaturized fabrication and dry storage.

Accordingly, in one aspect of the invention, a reference pH sensor is provided. The pH sensor is an extended gate field effect transistor (EGFET) structure, including a metal oxide semiconductor field effect transistor (MOSFET), an extended gate as a sensing unit including a substrate, a solid-state conductive sensing layer on the substrate, and a polypyrrole layer on the solid-state conductive sensing layer, and a conductive wire connecting the MOSFET and the sensing unit.

In a second aspect of the invention, a preparation of the reference pH sensor which is an extended gate field effect transistor (EGFET) structure is provided. The preparation includes the steps of providing an extended gate ion sensitive field effect transistor including an extended gate region, forming a solid-state conductive layer on the extended gate region to form a sensing unit, and forming a polypyrrole layer on the solid-state conductive layer by electro-polymerization to obtain a reference pH sensor.

The electro-polymerization can be performed by immersing the sensing unit in an electro-polymerizing solution, connecting the sensing unit to a positive electrode of a power supply, connecting a platinum electrode to a negative electrode of the power supply, and providing a constant potential from the power supply to perform electro-polymerization on the sensing unit.

In a third aspect of the invention, a system of measuring pH value in a solution is provided, The system includes a first pH sensor which is an extended gate field effect transistor (EGFET) structure; a second pH sensor as a reference electrode supplying stable voltage; a semiconductor characteristic instrument connecting the first and the second pH sensors respectively; a temperature controller including a temperature control center, a thermocouple, and a heater; and a light-isolation container isolating the sensing unit from the photo-sensitive effect. The first pH sensor includes a first metal oxide semiconductor field effect transistor (MOSFET), a first extended gate as a first sensing unit including a first substrate, and a first solid-state conductive sensing layer thereon, and a first conductive wire connecting the MOSFET and the sensing unit. The second pH sensor including a second metal oxide semiconductor field effect transistor (MOSFET), a second extended gate as a second sensing unit including a second substrate, a second solid-state conductive sensing layer on the second substrate, and a polypyrrole layer on the second solid-state conductive sensing layer, and a second conductive wire connecting the second MOSFET and the second sensing unit. The temperature control center connects the thermocouple and the heater, respectively.

Measurement of the pH value of a solution includes the steps of pouring a solution into the light-isolation container; immersing the first and the second sensing units, and the thermocouple in the solution; adjusting temperature of the solution by the heater controlled by the temperature control center after detecting temperature variation in the solution by the thermocouple; transmitting measurement data from the first and the second pH sensors to the semiconductor characteristic instrument; and reading out current-voltage (I-V) values of the solution by the semiconductor characteristic instrument to obtain pH value of the solution.

BRIEF DESCRIPTION OF THE DRAWINGS

The invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is the best determined by reference to the appended claims.

A reference pH sensor, the preparation and application thereof are provided.

Figure 1:
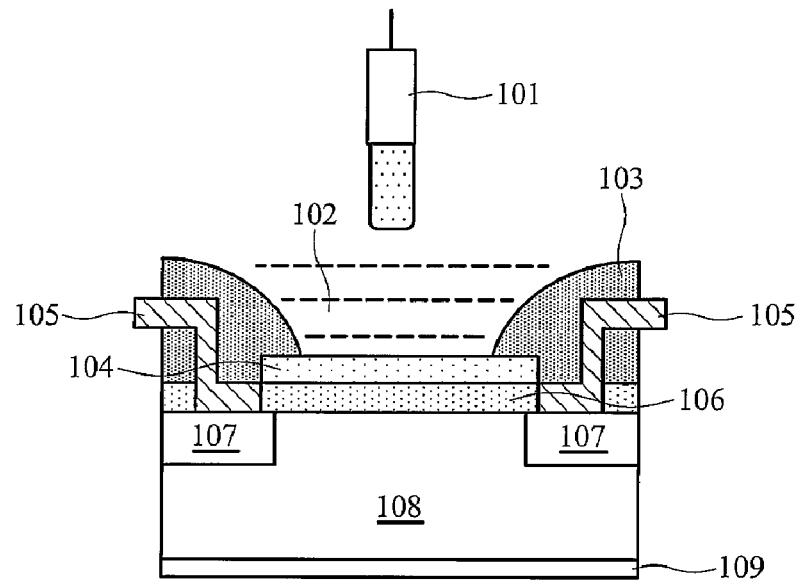
FIG. 1 shows a cross section of an embodiment of the pH sensor.

Referring to FIG. 1, a conventional ion sensitive field effect transistor (ISFET) comprises a p-type silicon substrate 108, a gate comprising a silicon dioxide film 106 on the substrate 108, and a sensing film 104 immobilized on the silicon dioxide film 106, wherein only the sensing film 104 directly contacts a test solution 102. Other elements of the ISFET are covered by an insulation region 103 comprising epoxy resin. The sensing film 104 can be $Al_2O_3$, $Si_3N_4$, $Ta_2O_5$, $WO_3$, a-Si:H, $SnO_2$, a-C:H, and the like. The sensitivity of the sensing film ranges from 50 to 58 mV/pH and the ISFET has highly sensitive linearity. Both sides of the silicon dioxide film 106 in the substrate are n-type heavy doped regions (source/drain) 107. A conductive wire 105, such as aluminum wire, connects the transistor such that source/drain electronic signals can be transmitted to additional circuits thereby after the test solution 102 is detected by the sensing film 104. In addition, a reference electrode 101 supplying stable voltage avoids noise disturbance. Detection by an ISFET is described below. First, the sensing film is exposed to an acidic or basic solution, and adsorbent hydrogen ions of the sensing film are converted to electronic signals. Threshold voltage of the ISFET is then controlled by the electronic signals. Finally, hydrogen ion concentration is obtained by examining current values. The sensing film can be a ruthenium oxide film prepared by radio frequency (RF) sputtering deposition. The sensitivity of the embodiment of the biosensor containing the ruthenium oxide film is 55.3 mV/pH and the biosensor has highly sensitive linearity and is suitable for the detection of the pH value in a solution.

In the example, the ruthenium oxide film was prepared by RF sputtering deposition with a gas mixture of argon and oxygen. The prepared ruthenium oxide film was used as a gate of a pH sensor and the sensitivity of the pH sensor was measured at various pH values. It was found that the sensitivity of the pH sensor has good linearity.

For the preparation of the embodiment of the novel planar solid-state reference electrode, the process combines semiconductor manufacture and polypyrrole electropolymerization process. Specifically, the reference pH electrode with low sensitivity was prepared by polypyrrole. The features of the polypyrrole can be adjusted by controlling the reaction conditions and pH sensor with various properties can be obtained. The reference electrode and the sensing electrode are prepared by ruthenium oxide which is a semiconductor membrane material, and a solid-state planar framework can be obtained. The embodiment of the reference sensor has the advantages of solid-state device, planar structure, dry storage, and easy manufacturing.

Figure 6:
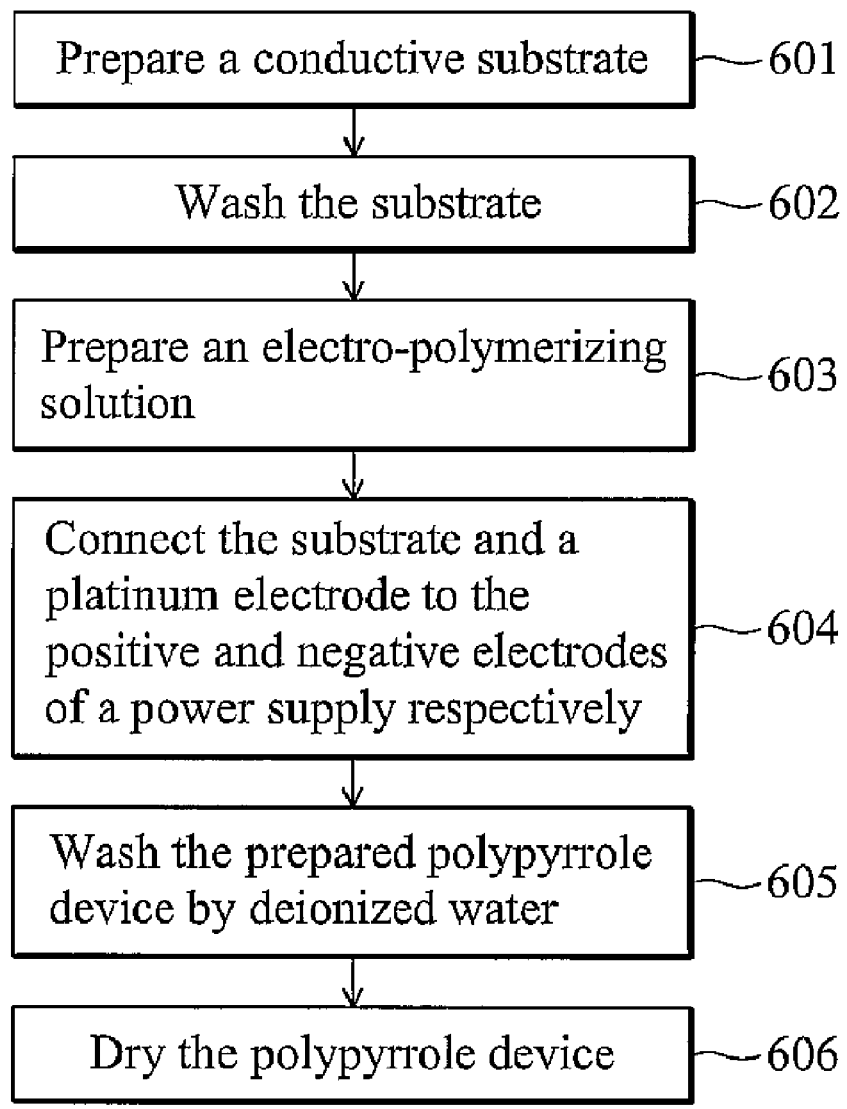
FIG. 6 shows a flowchart of the preparation of an embodiment of the reference pH sensor.

The preparation of the planar solid-state reference electrode includes the steps of depositing a solid-state conductive membrane on a substrate by a semiconductor coating technology, and polymerizing a polypyrrole membrane on the conductive membrane by electrochemical polymerization. A flowchart of the preparation is shown in FIG. 6. In step 601, a clean substrate is provided. The substrate can be silicon, glass, ceramics, or plastics, preferably silicon substrate. A conductive sensing thin film is formed on the substrate, for example, by sputtering a ruthenium oxide film. The device is sealed with an insulating material, such as epoxy resin, and an sensing window is exposed. In step 602, the substrate is washed. In step 603, an electro-polymerizing solution is prepared. The electro-polymerizing solution includes phosphates, potassium chloride, and pyrrole. The combination of the electro-polymerizing solution can be adjusted to control the sensitivity of the polypyrrole membrane. In step 604, the device is immersed in the electro-polymerizing solution and connected to a positive electrode of a power supply. A platinum electrode is connected to a negative electrode of the power supply. A constant potential is provided to form a polypyrrole thin film on the substrate. In step 605, the device is dried and a polypyrrole/$RuO_X$ reference electrode is obtained.

Accordingly, one embodiment of a reference pH sensor is an extended gate field effect transistor (EGFET) structure, including a metal oxide semiconductor field effect transistor (MOSFET), an extended gate as a sensing unit including a substrate, a solid-state conductive sensing layer on the substrate, and a polypyrrole layer on the solid-state conductive sensing layer, and a conductive wire connecting the MOSFET and the sensing unit.

One embodiment of the preparation of the reference pH sensor which is an extended gate field effect transistor (EGFET) structure includes the steps of providing an extended gate ion sensitive field effect transistor including an extended gate region, forming a solid-state conductive layer on the extended gate region to form a sensing unit, and forming a polypyrrole layer on the solid-state conductive layer by electro-polymerization to obtain a reference pH sensor.

In one embodiment of the preparation, the metal-oxide semiconductor field effect transistor (MOSFET) is an N-type FET. The conductive wire connects the gate of the MOSFET and the sensing unit. The substrate can be silicon, glass, ceramic, or plastic, preferably a silicon substrate. The solid-state conductive sensing film can be any conductive film, preferably a ruthenium oxide film. In addition, the reference pH sensor further comprises an insulating layer covered the sensing unit, wherein the insulating layer is epoxy resin.

In another embodiment of the preparation, the electro-polymerization can be performed by immersing the sensing unit in an electro-polymerizing solution, connecting the sensing unit to a positive electrode of a power supply, connecting a platinum electrode to a negative electrode of the power supply, and providing a constant potential from the power supply to perform electro-polymerization on the sensing unit. The electro-polymerizing solution includes phosphates, potassium chloride, and pyrrole. The ratio of the components is phosphate:potassium chloride:pyrrole=0.1M:001M:0.15~0.5M, preferably 0.1M:0.01M:0.3~0.5M, more preferably 0.1M:0.01M:0.3M. The constant potential is 4V.

One embodiment of the system of measuring pH value in a solution includes a first pH sensor which is an extended gate field effect transistor (EGFET) structure; a second pH sensor as a reference electrode supplying stable voltage; a semiconductor characteristic instrument connecting the first and the second pH sensors respectively; a temperature controller including a temperature control center, a thermocouple, and a heater; and a light-isolation container isolating the sensing unit from the photosensitive effect. The temperature control center connects the thermocouple and the heater, respectively.

In one embodiment of the measuring system, the first pH sensor includes a first metal oxide semiconductor field effect transistor (MOSFET), a first extended gate as a first sensing unit including a first substrate, and a first solid-state conductive sensing layer thereon, and a first conductive wire connecting the first MOSFET and the first sensing unit. The second pH sensor includes a second metal oxide semiconductor field effect transistor (MOSFET), a second extended gate as a second sensing unit including a second substrate, a second solid-state conductive sensing layer on the second substrate, and a polypyrrole layer on the second solid-state conductive sensing layer, and a second conductive wire connecting the second MOSFET and the second sensing unit. The first and second metal-oxide semiconductor field effect transistor (MOSFET) can be an N-type FET. The first and second substrate can be a silicon substrate. The first and second solid-state conductive sensing film can be a ruthenium oxide film. In addition, the first and second pH sensors further comprise an insulating layer covering their sensing unit, wherein the insulating layer is epoxy resin.

Measurement of the pH value of a solution includes the steps of pouring a solution into the light-isolation container; immersing the first and second sensing units and the thermocouple in the solution; adjusting temperature of the solution by the heater controlled by the temperature control center after detecting temperature variation in the solution by the thermocouple; transmitting measurement data from the first and the second pH sensors to the semiconductor characteristic instrument; and reading out current-voltage (I-V) values of the solution by the semiconductor characteristic instrument to obtain pH value of the solution. The semiconductor characteristic instrument is Keithley 236. The light-isolation container is a dark box.

The miniaturized electrode still requires a reference electrolyte and the step of pouring the reference electrolyte into the electrode is difficult. With the embodiment of the planar solid-state reference electrode, the electrolyte pouring step is unnecessary. In addition, the embodiment of the planar solid-state reference electrode may substitute the Ag/AgCl reference electrode. Moreover, the components of the electro-polymerizing solution can be adjusted to control the sensitivity of the polypyrrole sensor. This can be applied as counter-sensing electrodes or differential electrodes.

Practical examples are described herein.

EXAMPLE

Example 1

Preparation of a Ruthenium Oxide Sensing Film

The ruthenium oxide film ($RuO_x$) was applied as the pH sensing film in one embodiment of the pH sensor. The ruthenium oxide film was deposited on a silicon wafer by radio frequency (RF) sputtering with a ruthenium target of a purity of 99.99%. Specifically, a p-type (100) silicon substrate was washed with buffer oxide etching (BOE) solution to remove contaminants from the surface thereof. The residue on the substrate was removed with nitrogen spray. Before the deposition, the pressure of the reaction chamber was maintained at least $10^{-6}$ torr. The mixture of $Ar/O_2$ was introduced into the reaction chamber with a flow rate of Ar=40 sccm and $O_2$=15 sccm and a pressure of 10 mtorr. Deposition power was 100 W. Pre-sputtering was performed for 10 minutes to remove unwanted oxides on the surface of the ruthenium target. The ruthenium oxide film was formed on the silicon substrate after 30-min sputtering, and the sensing unit deposited with a ruthenium oxide film was obtained.

The sensing unit was covered by epoxy resin (EPO-TEK H77 lid sealing epoxy), exposing partial ruthenium oxide film to form a sensing window. The sensing unit was connected with a gate of a MOSFET by an aluminum wire. The process of the sealing was described below. The prepared sensing film was cut into a size of 1.5 cm×1.5 cm and washed by deionized water in an ultrasound cleaner. An aluminum wire was fixed to the sensing film by Ag paste and the sensing unit was baked at 120° C. for 10 minutes. Epoxy resin was applied to the sensing unit and the sensing unit was baked again at 120° C. for 20 minutes. The aluminum wire was passed through a capillary and the whole sensing unit was sealed with epoxy resin to leave a window of 2 mm×2 mm. The sensing unit was then baked at 120° C. for 20 minutes and the extended ruthenium oxide sensing unit was obtained.

Example 2

Preparation of a Planar Solid-State Reference Electrode

A planar solid-state reference electrode was prepared in combination of the semiconductor manufacture and the polypyrrole polymerization process. The procedure was conducted as shown in FIG. 6. A ruthenium oxide film was prepared according to Example 1, and a polypyrrole film was formed on the ruthenium oxide film as described below.

Figure 5:
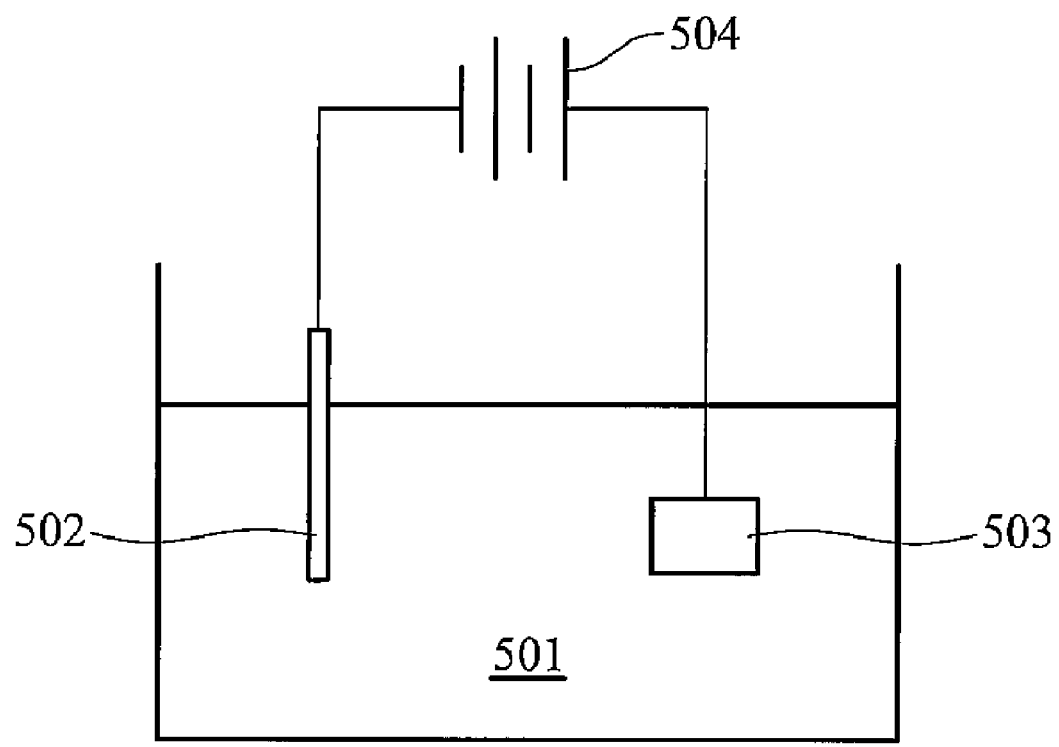
FIG. 5 shows an electro-polymerization system of polypyrrole on an embodiment of the reference pH sensor.

As shown in the flowchart of FIG. 6, a clean $RuO_x$/Si substrate was provided (step 601). Materials were chosen based on the surface conductivity property. The $RuO_x$/Si substrate was washed (step 602). An electro-polymerizing solution was then prepared (step 603). The electro-polymerizing solution included phosphates, potassium chloride, and pyrrole. The electro-polymerization was performed according to the system shown in FIG. 5. The $RuO_x$/Si substrate 503 was immersed in the electro-polymerizing solution 501 and connected to a positive electrode of a power supply. A platinum electrode 502 was connected to a negative electrode of the power supply. A constant potential 504 which is higher than the oxidation potential of polypyrrole, such as 4V, was provided for 30 minutes to form a polypyrrole thin film on the substrate (step 604). The device was immersed in deionized water for 10 minutes (step 605) and dried (step 606), and a polypyrrole/RO$_X$ reference electrode was obtained.

Figure 7:
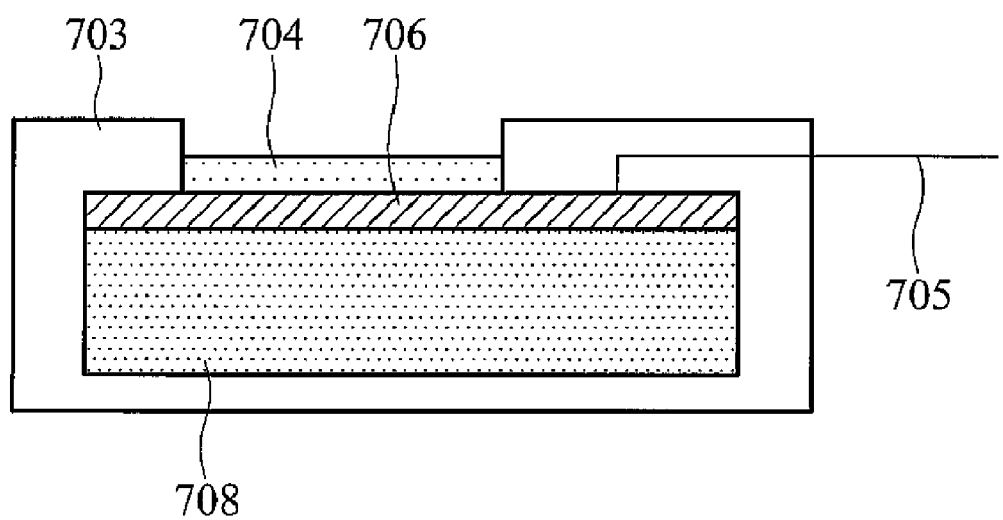
FIG. 7 shows an extended region of an embodiment of the reference pH sensor.

The obtained polypyrrole/RO$_X$ reference electrode was as shown in FIG. 7. A ruthenium oxide film 706 was formed on a silicon substrate 708, and a polypyrrole film 704 was formed on the ruthenium oxide film 706. A conducting wire 705, such as aluminum wire, connected the polypyrrole/RO$_X$ reference electrode to an MOSFET. The device was packaged with epoxy resin 703.

Example 3

Measurement of Sensitivity

Figure 2:
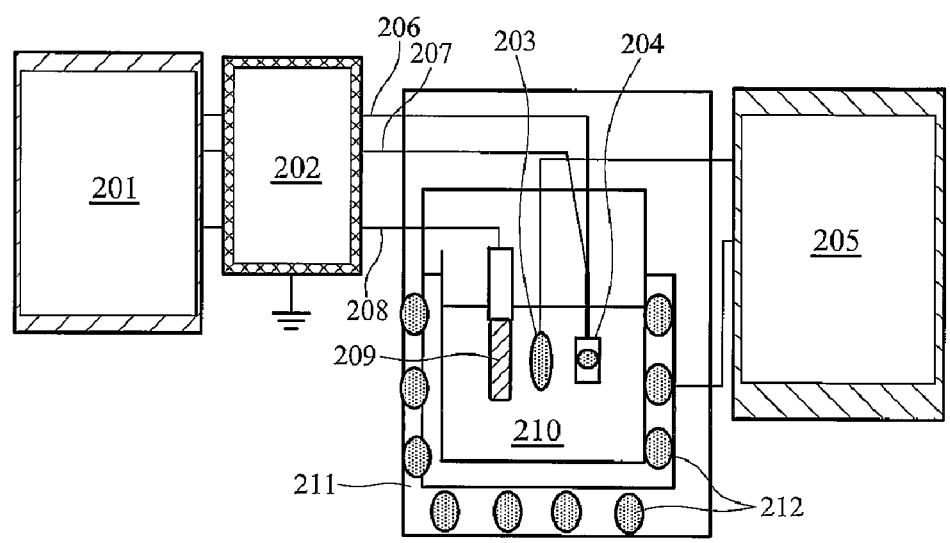
FIG. 2 shows a current-voltage measuring system for the measurement of the sensitivity of an embodiment of the pH sensor.

Sensitivity of the pH sensor was determined with the current-voltage measuring system as shown in FIG. 2. A sensing unit 204 and the prepared reference electrode 209 were immersed in a test solution 210 which was placed in a dark box 211 to exclude the influence of light and temperature. The wires connected to the source 207 and the drain 206 of a commercialized IC (CD4007UB) and the reference electrode 208 were linked to a testing end 202 which links to a semiconductor characteristic instrument Keithley 236 source measure unit 201. The wire connected to the gate of the commercialized IC was linked to the sensing unit 204. Three Keithly 236 were applied where the first was lined to the source/drain of the IC to provide a suitable bias voltage, the second was linked to the reference electrode, and the third was linked to the drain. The temperature of the solution 210 was controlled by a PID temperature controller 205.

Figure 3:
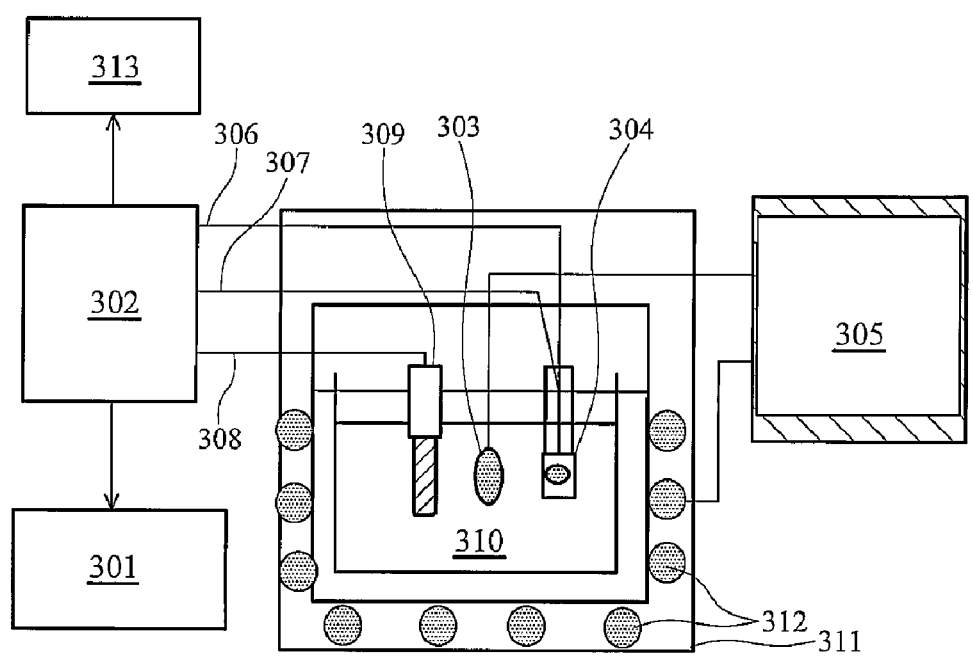
FIG. 3 shows a constant voltage constant current (CVCC) measuring system for the measurement using an embodiment of the pH sensor.
Figure 4:
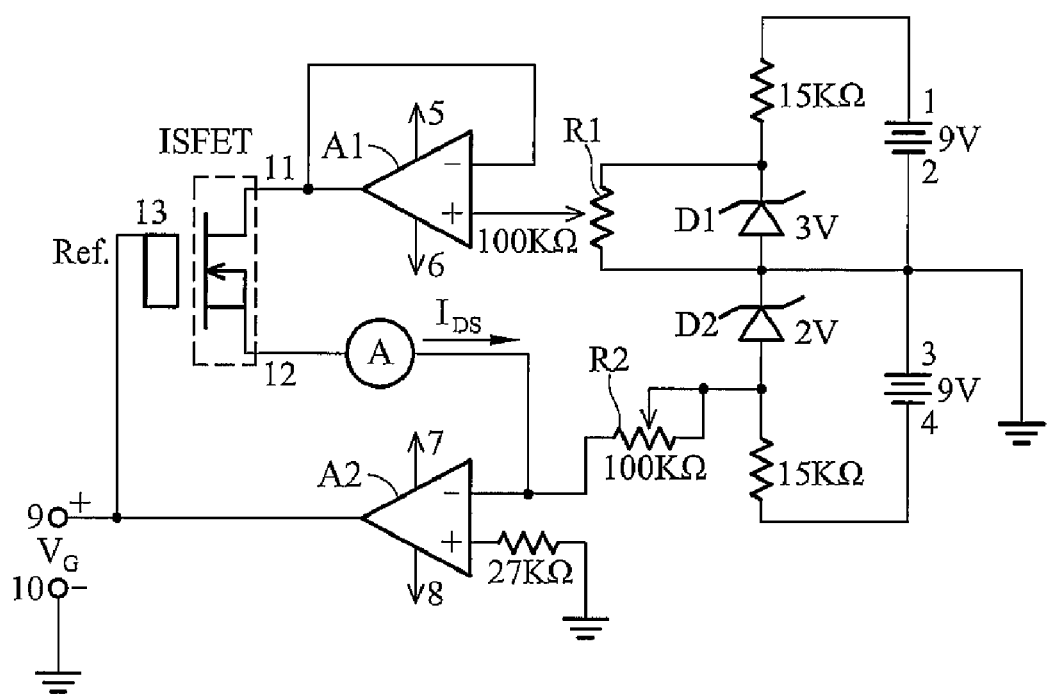
FIG. 4 shows a constant voltage constant current (CVCC) circuit for the measurement using an embodiment of the pH sensor.

A constant current constant voltage (CCCV) measuring system as shown in FIG. 3 was applied. The sensing unit 304, the reference electrode 309, and the thermocouple 303 were immersed in a test solution 310. When the thermocouple 303 detects an altered temperature of the test solution 310, the temperature controller 305 may drive the heaters 312 to adjust the test solution temperature to a fixed temperature, 25° C. The measurement of the sensing unit 304 and the reference electrode 309 can be transmitted to the semiconductor characteristic instrument 302, and the pH value of the test solution 310 can be read therefrom. The wiring structure of this system was similar to the system of FIG. 2, wires connected to the source 307 and the drain 306 of a commercialized IC (CD4007UB) and the reference electrode 309 were linked to a testing end 302 which links to a semiconductor characteristic instrument Keithley 236 source measure unit 301. The Keithley 236 (301) linked to a voltage-time recorder 313 to process the signals. The circuit system of the CCCV measuring system was as shown in FIG. 4.

The method of measuring the sensitivity of a pH sensor using the above-mentioned system is described in the following. Keithley 236 was set as: $V_{DS}$=0.2V. The initial gate voltage was $V_G$=0.5V, increased 0.2V each time, and the final gate voltage was $V_G$=5V.

The sensing film was immersed in the test solution for 1.5 minutes to balance the temperature between the sensing film and the test solution.

Figure 8:
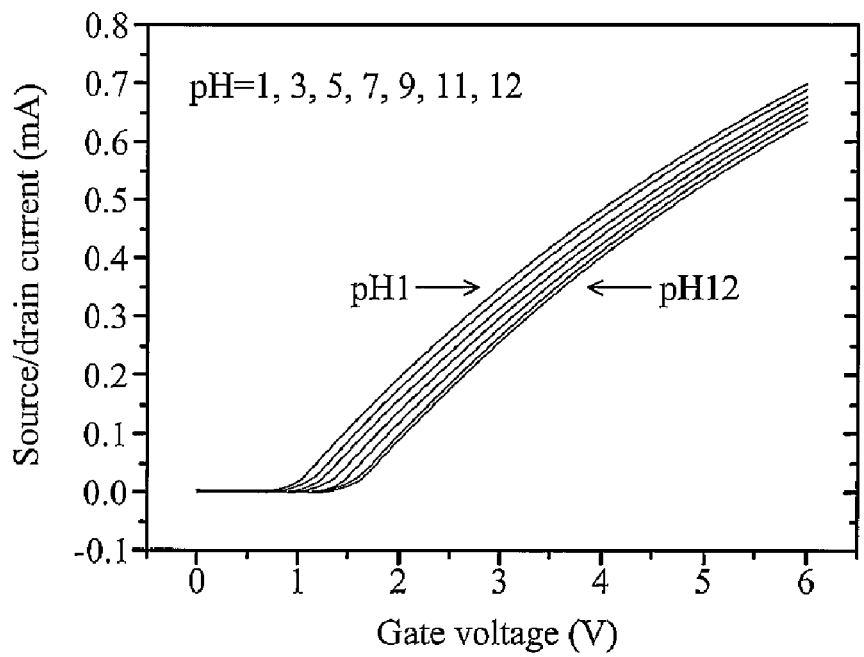
FIG. 8 shows source/drain current-gate voltage curve of an embodiment of the pH biosensor under various pH values at 25° C.
Figure 9:
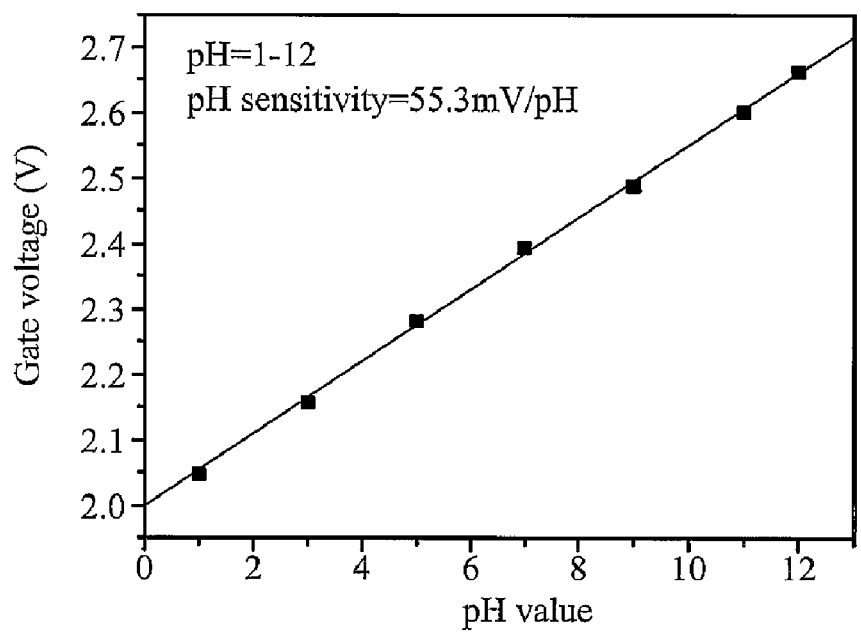
FIG. 9 shows a gate voltage-pH curve of an embodiment of the pH biosensor under various pH values at 25° C.

The curves of source/drain current versus gate voltage of the pH sensor in solutions with pH 1~pH12 at 25° C. were shown in FIG. 8. The calibration curve of gate voltage versus pH value of the pH sensor at 25° C. was shown in FIG. 9. The slope of the curve indicates that the pH sensor has a sensitivity of 55.3 mV/pH. This result proved that the pH sensor containing the ruthenium oxide film is suitable for the measurement of pH value in aqueous solutions.

Figure 10:
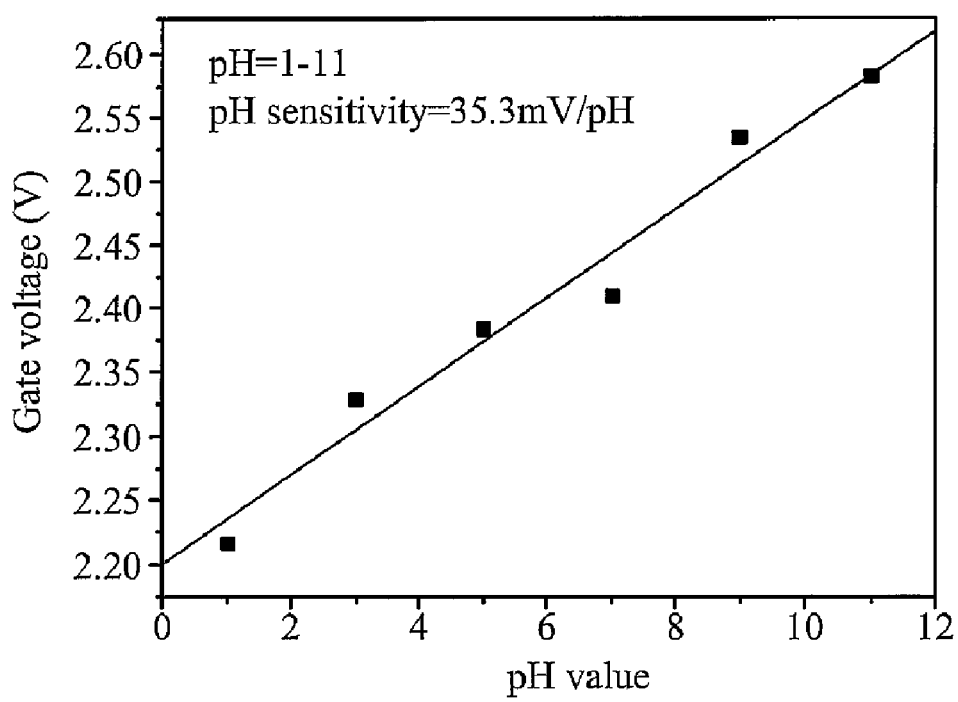
FIG. 10 shows a gate voltage-pH curve of an embodiment of the reference pH sensor.

The calibration curve of gate voltage versus pH value of the reference pH sensor at 25° C. was shown in FIG. 10. The slope of the curve indicates that the reference pH sensor has a lower and stable sensitivity of 35.3 mV/pH. This result proved that the embodiment of the reference pH sensor is suitable to be a counter electrode to achieve differential structure of the pH sensors.

As described above, the reference pH sensor has a lower and more stable sensitivity than the pH sensor of the ruthenium oxide film. In addition, the reference pH sensor has a solid-state planar structure and has the advantages of dry storage and easy manufacturing.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A system of measuring pH value in a solution, comprising a first pH sensor which is an extended gate field effect transistor structure, comprising:
    a first metal oxide semiconductor field effect transistor (MOSFET);
    a first extended gate as a first sensing unit, comprising a first substrate, and a first solid-state conductive layer thereon; and
    a first conductive wire connecting the first MOSFET and the first sensing unit.
    a second pH sensor as a reference pH sensor supplying stable voltage, comprising:
    a second metal oxide semiconductor field effect transistor (MOSFET);
    a second extended gate as a second sensing unit, comprising a second substrate, a second solid-state conductive layer thereon, and a polypyrrole layer on the second solid-state conductive layer; and
    a second conductive wire connecting the second MOSFET and the second sensing unit;
    a semiconductor characteristic instrument connecting the first pH sensor and the second pH sensor respectively;
    a temperature controller comprising a temperature control center, a thermocouple, and a heater, wherein the temperature control center connects the thermocouple and the heater, respectively; and
    a light-isolation container isolating the sensing unit of the second pH sensor from photosensitive effect;
    wherein measurement of pH value of a solution comprising:
    pouring a solution into the light-isolation container;
    immersing the sensing unit of the first and the second pH sensors, and the thermocouple in the solution;
    adjusting temperature of the solution by the heater controlled by the temperature control center after detecting temperature variation in the solution by the thermocouple;
transmitting measurement data from the first and the second pH sensors to the semiconductor characteristic instrument; and
    reading out current-voltage (I-V) values of the solution by the semiconductor characteristic instrument to obtain pH value of the solution.

2. The system as claimed in claim 1, wherein the first and the second MOSFETs are n-type.

3. The system as claimed in claim 1, wherein the first and the second substrates are silicon.

4. The system as claimed in claim 1, wherein the first and the second solid-state conductive layers are ruthenium oxide.

5. The system as claimed in claim 1, wherein the first and the second sensing units further comprises an insulating layer covered on the sensing units.

6. The system as claimed in claim 5, wherein the insulating layer is epoxy resin.

7. The system as claimed in claim 1, wherein the semiconductor characteristic instrument is Keithley 236.

8. The system as claimed in claim 1, wherein the light-isolation container is a dark box.

* * * * *